United States Patent [19]
Prentiss

[11] Patent Number: 5,993,479
[45] Date of Patent: Nov. 30, 1999

[54] INFANT FEEDING CONTAINER

[76] Inventor: John G. Prentiss, P.O. Box 15458, Santa Fe, N.Mex. 87506-5458

[21] Appl. No.: 08/974,718

[22] Filed: Nov. 19, 1997

Related U.S. Application Data

[63] Continuation-in-part of application No. 07/814,565, Dec. 30, 1991, Pat. No. 5,690,679.

[51] Int. Cl.$^6$ .................................................. A61J 17/00
[52] U.S. Cl. ........................................ 606/236; 215/11.6
[58] Field of Search ................................... 606/234–236; 128/848, 859; 215/11.6, 100

[56] References Cited

U.S. PATENT DOCUMENTS 3,112,837  12/1963  Manoyian .

*Primary Examiner*—Michael A. Brown
*Attorney, Agent, or Firm*—DeWitt M. Morgan, Esq.

[57] ABSTRACT

An infant feeding container is disclosed which attempts to imitate a human female breast in form and function. The container comprises a dome shaped member including a pliant outer surface. The dome shaped member substantially defines a volumetric space adequate to contain from four to eleven ounces of liquid and has the approximate form of a human female breast. The dome portion includes an upper crest and a lower skirt, the skirt portion being not less than seven centimeters in diameter at its outermost circumference. A ducted nipple protrudes from the crest of the dome and a bottom closure is secured to the dome portion adjacent to the skirt portion. Included are double and triple wall embodiments, a unique removable liner, optional means to couple the container to a conventional breast pump, an anti-vacuum feature, thermographic means to warn against overheated contents, and jackets in infant friendly materials.

20 Claims, 3 Drawing Sheets

FIG. 1-A

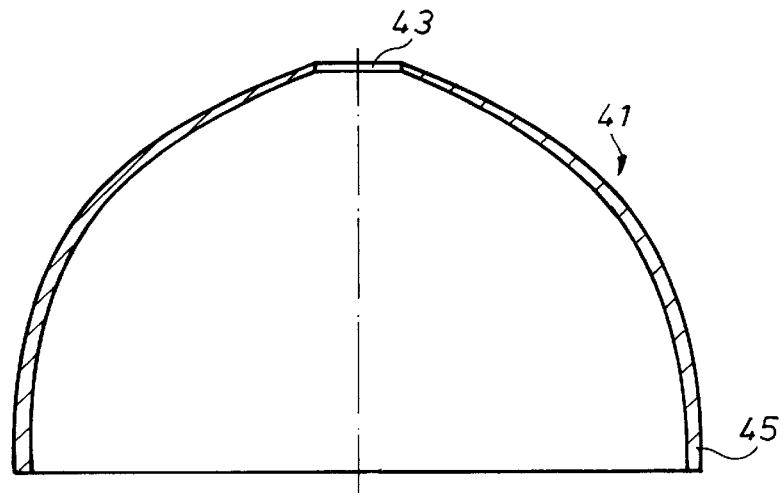
FIG. 3
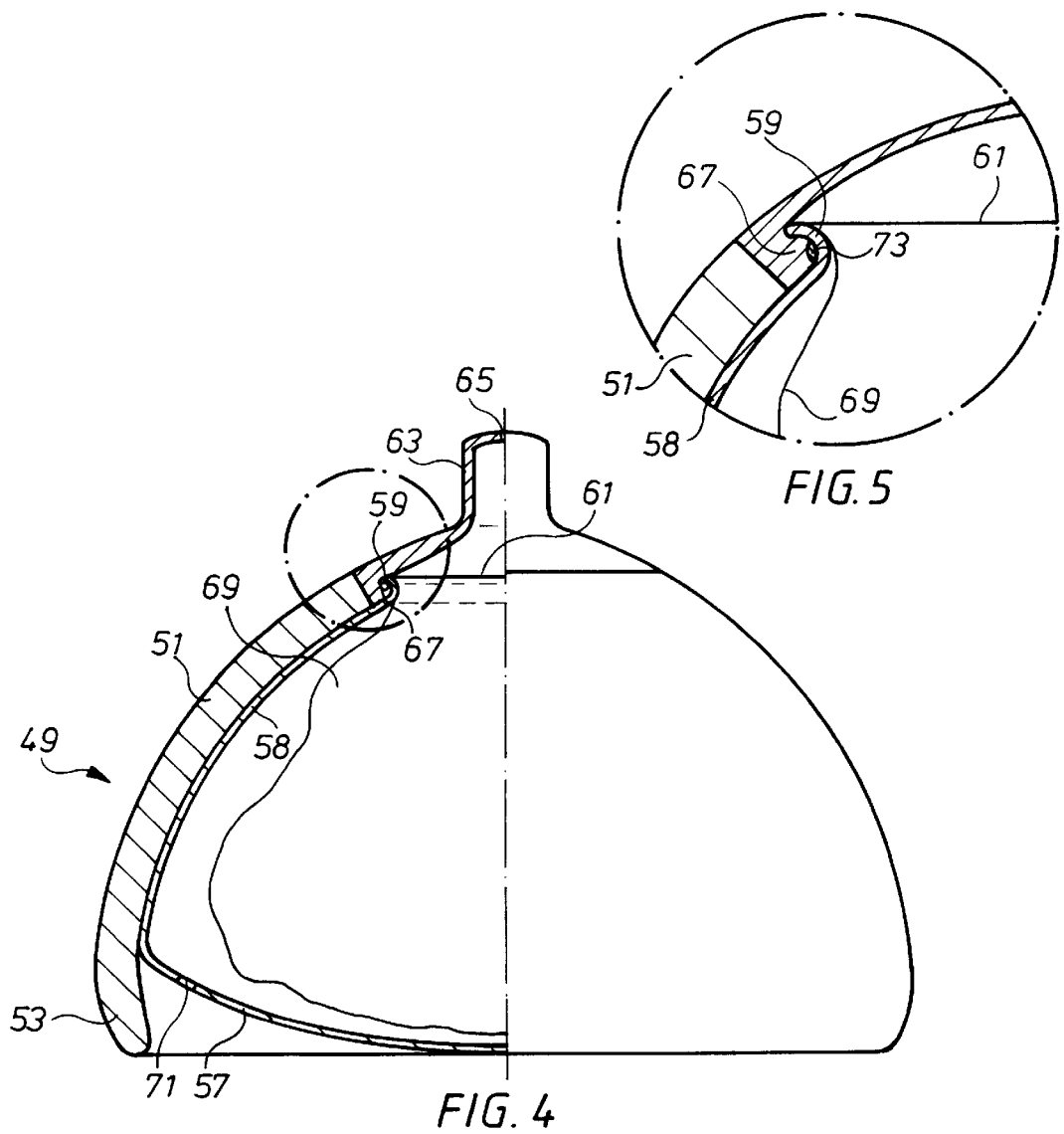
FIG. 5
FIG. 4

INFANT FEEDING CONTAINER

This is a continuation-in-part of U.S. patent application Ser. No. 07/814,565, filed Dec. 30, 1991 now U.S. Pat. No. 5,690,679. Disclosed herein are certain embodiments of a breast like infant feeding container which posses the basic advantages of the invention of the earlier application, while including further advantages which will become apparent from the disclosures herein.

FIELD OF INVENTION

The present invention relates to infant feeding containers, more specifically to one which has the approximate form, feel, and finction of a natural breast.

BACKGROUND

It is widely known that natural breast feeding is the best way to nurture an infant. The quality of mother's milk is superior to prepared formulas and the act of providing an infant with the mother's warm breast and comfort is an important aspect of proper child development and bonding between mother and infant. However, artificial feeding systems may be desirable or necessary in some circumstances. These include medical situations such as premature births, mothers who have had mastectomies or who are unable to lactate sufficiently, infants who require dietary supplements, and health problems such as cleft pallet or breast abscesses. Social situations requiring artificial feeding include employed women who are unable to feed their infant at work, women who use a breast pump and require a container for feeding, the need to feed adopted infants, and other medical or social situations that may recommend the use of an artificial container.

Healthcare professionals agree that an infant's sensory experience is particularly important in the formidable stages of development, and especially in the feeding process. While artificial feeding containers can never fully imitate a mother, the breast-like infant feeding container disclosed in U.S. patent application Ser. No. 07/814,565 provides a far more natural sensory experience for infants when artificial feeding means are needed.

The many baby bottles now widely in use may be cited for abundant shortcomings, the greatest being the unnaturalness of nursing from a rigid, angular, elongate container, often in contact with an infant's cheeks, chin, nose and hands. This results in a predominance of unnatural sensory experience that is inappropriate, particularly for newborn infants. Although artificial nipples are typically soft, they do not provide a sensory experience similar to the comforting feeling of breast feeding wherein an infant is often in fill contact with the mother's soft, warm breast. A second disadvantage is that elongate bottles have a small base and a high center of gravity, making them vulnerable to overturning. Elongate bottles are hard to clean, as the bottom may be reached only with a bottle brush. Furthermore, rigid bottles can cause infants to ingest unnecessary amounts of air. While the latter issues are addressed by recent innovations in infant feeding systems, no existing container, other than the one referenced in patent application Ser. No. 07/814,565, offers the combination of form, feel and function comparable to natural breast feeding.

Manoyian, U.S. Pat. No. 3,112,837, discloses a disposable bulbous infant feeding container which has rigid elements in contact the infant's mouth. The unit was designed to be sold with dry formula, the user adding water and discarding the container after one use. The container cannot be filled with breast milk, washed or refilled. Furthermore, it has a high center of gravity and a narrow base. These deficiencies appear to have precluded commercial success.

Manufacture of a breast imitating container is dependent on the use of non-toxic, hypoallergenic materials which are safe for use in the subject application, easily molded, cost effective, and have good tactile surface quality. Preferred embodiments are disclosed which improve the performance of the breast like container previously in patent application Ser. No. 07/814,565, and facilitate cost effective manufacture.

Removable liners have been in common use in infant feeding containers for many years. However, the use of a removable liner in a breast like container presents unique problems. Of particular importance is the tactile quality of the upper part of the container which comes in frequent contact with the infant's face. Also, the filling port on a collapsible liner must be small enough to allow the liner to collapse, permitting the full contents to be withdrawn. For these reasons, the liner of the present invention is designed to eliminate the usual rigid components used to seal the top of conventional elongate liners, as these components are typically in contact with an infant's mouth, chin, nose and cheeks.

The ingestion of air by an infant using an artificial container is believed to be a major contributor to colic. While a resilient container helps to mitigate this problem, embodiments of the breast like container have been designed to include an integral anti-vacuum valvular feature to further reduce the incidence of air ingestion by the infant user.

A four piece container design is also disclosed herein to facilitate more cost effective molding and to improve sealability of the bottom closure lid on certain embodiments.

Resilient foams can provide good tactile surface quality, but limitations exist with these materials relative to their ability to provide a sealable structure to withstand the abuse imposed by infant usage, such as dropping a full container from a crib or high chair. Bonding rigid elements to a foam container body to overcome this problem is one option. Alternately, non-foam thermoplastics and thermoset rubber can be molded with sealable threads when molded with an adequate cross section. These same materials have good resilience and tactile quality when molded in thin cross section so that a single container can be both relatively rigid at the base and pliant in the upper nipple area depending upon container wall thickness.

It has become evident that the breast-like container will often be used in conjunction with a breast pump to provide an infant with expressed mother's milk. To obviate the need for an adapter, an intermediate container, or a modified container attachment on standard breast pumps, it is desirable to be able to directly couple the breast like container of the present invention with a conventional breast pump.

Constraints in molding processes, combined with the current availability of tear resistant, resilient foams which are approved for food contact, led to design approaches that offer excellent surface tactile quality as well as possessing insulating value to retain warmth of the contents over an extended feeding period.

The above identified pending application specifies resilient container walls to simulate the tactile quality of a natural breast. Many types of foam, and particularly those more recently developed, conform to the original criteria to a high degree. Fine grained cellular thermoplastic elastomers, metallocene polyolefins, elastomeric metallocene rubber as well as other types of foamed thermoplastics and rubber can provide a safe, hypoallergenic and non-toxic container having excellent tactile quality, good thermal insulation properties, and a satisfactory degree of tear resistance. Furthermore, a relatively rigid inner shell may be used beneath the foam to mitigate potential problems with leakage through the nipple when the container is squeezed. Specification of the use of resilient foams in the container facilitates constructing a breast-like infant feeding container having friendly tactile quality, of considerable importance in the subject invention.

OBJECTS AND ADVANTAGES

A first object of the present invention is the fabrication of a breast like infant feeding container employing advanced materials and technology to insure optimum performance of the product. A second object is to provide a breast shaped infant feeding container carrying a removable and optionally disposable containment liner for liquid contents. A third object is to enable a breast shaped container to be readily used with a breast pump without requiring an independent adapter, a modified container-specific breast pump, or intermediate container for expressed milk. A fourth object is to provide an anti-vacuum feature in certain embodiments. A fifth object is to disclose presently preferred approaches to design and manufacture in order to effect cost savings in the manufacture of the product. A sixth object is to provide a breast like infant feeding container with thermographic means to warn against overheating. A seventh object is to provide a breast shaped container having an optional jacket for improved tactile quality and warmth.

SUMMARY OF THE INVENTION

In accordance with the present invention, an infant feeding container substantially imitating the form, feel and function of a natural breast comprises a breast like dome configuration having pliant surface quality and a nipple at the crest of the dome. The container may be embodied as a bottom filling or top filling unit. Optional features include a removable liner, provision for direct attachment to a breast pump, an anti-vacuum component, means to warn against overheated contents, and infant friendly jackets on the exterior.

BRIEF DESCRIPTION OF THE DRAWINGS

FIG. 3 shows a cross section of a foam jacket for the container of FIG. 1;

FIG. 4 is a partial section of a top filling embodiment of the present invention having a removable compression fit nipple, and a foam outer dome;

FIG. 5 is an enlarged detail of the nipple engagement mechanism of FIG. 4;

DETAILED DESCRIPTION OF THE DRAWINGS

Figure 1:
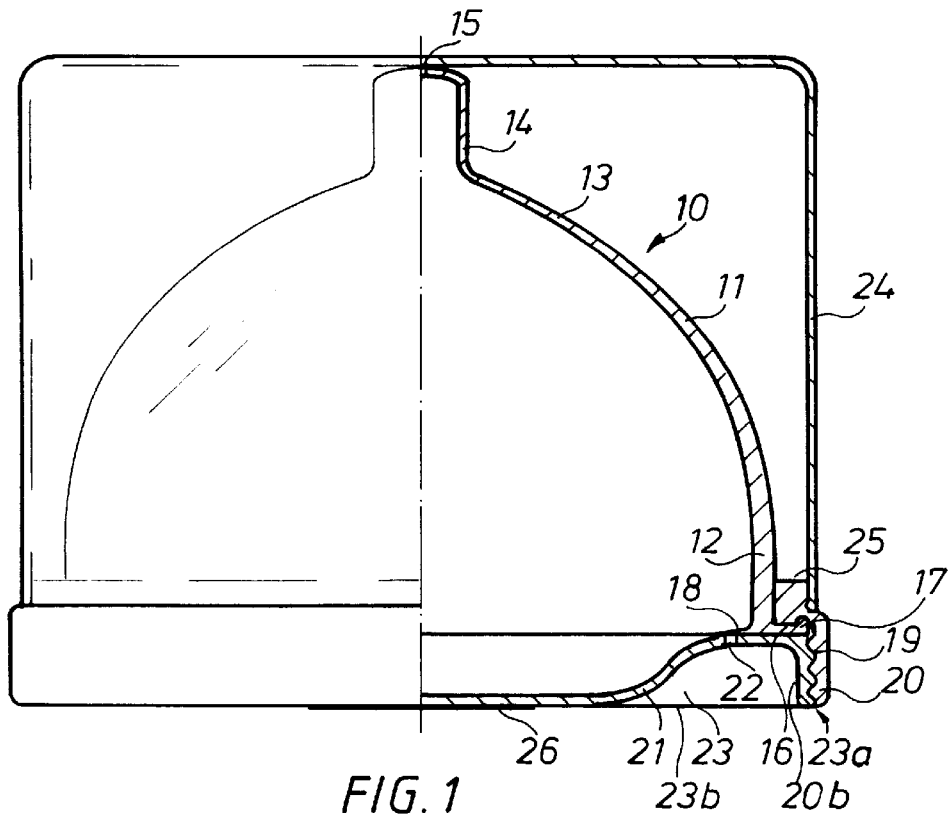
FIG. 1 is a partial cross section of a four piece embodiment of the present invention with threaded base lid and nipple cap.
Figure 2:
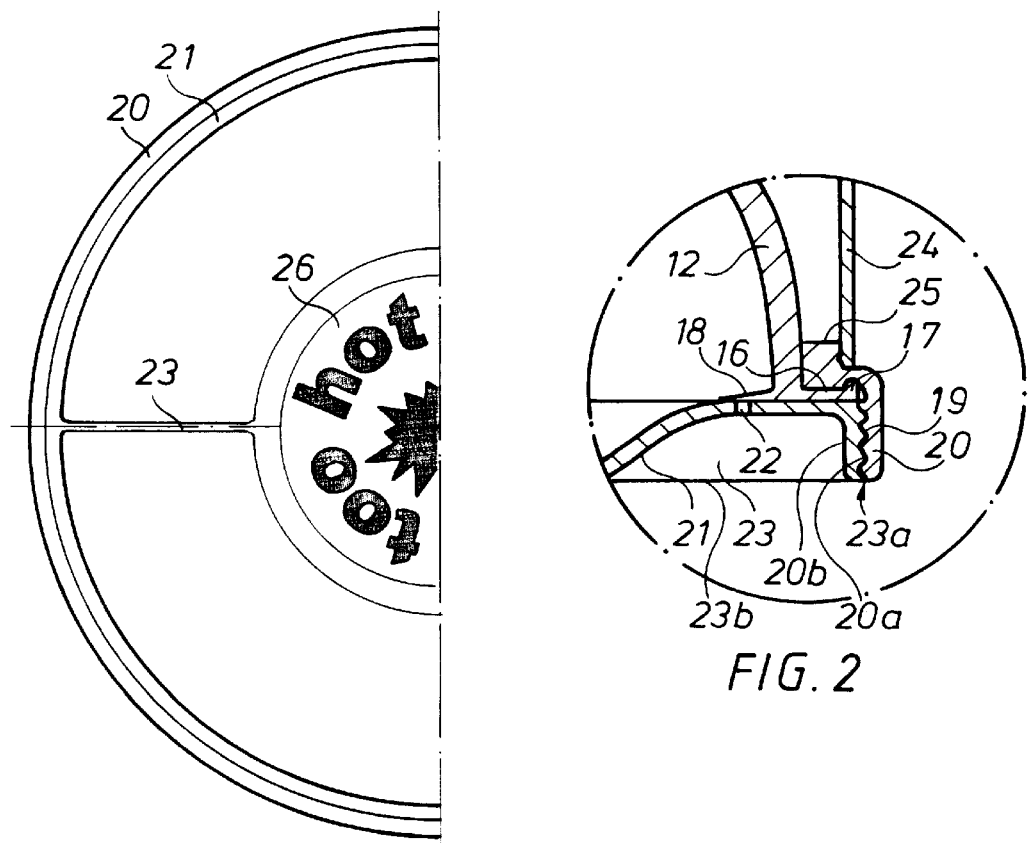
FIG. 2 is a detail of FIG. 1.

FIG. 1 is a cross section of a four piece embodiment molded in an elastomer such as silicone rubber, latex, Santoprene®, Pellethane® or other suitably pliant material. Container 10 includes a dome shaped member 11 which is injection molded in varying thickness to provide stability in the lower or skirt portion 12 and a soft resilient surface in the upper crest portion 13 near nipple 14 with duct(s) 15. Dome shaped member 11 is equipped with outer flange 16, annular rib 17 and valvular flange 18 which is slightly turned down (i.e. away from the nipple) when disengaged. Threads 19 in ring 20 engage corresponding threads 20A on lip 20B of lid 21. Lid 21 may include one or more small air vents 22 and is recessed at 23 near the outer circumference to provide an annular gripping portion defined 23A by ring 20 and lip 20B. Integral webs 23B provide easy turning means for threaded lid 21. Cap 24 is formed of thermoplastic, secures over an annular protrusion 25 on ring 20, and is sized so as to simultaneously close nipple ducts 15 against leakage when cap 24 is installed. Cap 24 may serve as a base when filling the container and may be marked with gradations for use as a measuring device. A warning message "Too Hot" (not shown) is printed on lid 21, over which a thermographic masking ink 26 is applied. The mask is opaque below approximately 98F, becoming quickly transparent to reveal the warning message when heated above the design temperature.

In operation, dome 11 is inserted through ring 20 until annular rib 17 engages a corresponding annular detent in ring 20 to prevent rupture during use. Cap 24 is installed on ring 20 so as to seal nipple ducts 15. The container is inverted, filled with liquid, and lid 21 is turned by webs 23 to screw threads 20A into threads 19, whereupon outer flange 16 seals the contents and valvular flange 18 closes air vents 22 with a pressure of approximately 5 psi. When the user infant withdraws liquid from ducts 15 and internal vacuum is thus created, valvular flange 18 lifts until incoming air equalizes the vessel's internal pressure to close air vents 22.

FIG. 3 discloses a compression molded foam jacket 41 formed to jacket container 10 of FIG. 1. Manufacturers of pliant foamed polyethylene products found to be good for this application are Zotefoam, Inc., Hackettstown, N.J., Sentinel Products Corp., Hyannis, Mass., and Voltek, Ft. Worth, Tex. Jacket 41 includes an upper opening 43 through which nipple 14 of FIG. 1 is inserted. Lower portion 45 may be slightly turned in to provide a grip on the skirt portion 12. Other materials appropriate to this application include animal hide, quilted down, cotton, polyester, fleece or other natural or synthetic jacketing material having a friendly tactile quality. In non-foam embodiments, jackets may be provided with an independent drawstring, elastic member (not shown) at the lower portion 45, or other suitable means to secure the jacket 41 in place.

FIG. 4 discloses a top filling embodiment of the present invention 49 having an outer dome 51 formed in the approximate shape of a human female breast and constructed of a thermoformed or compression molded fine celled, resilient foam as in FIG. 3. The extended lower portion 53 of outer dome 51 is molded to constitute an annular gripping member for the infant and care giver. Bottom closure 57 is molded integrally with inner dome 58 and hook ring 59 which defines filling port 61. Nipple 63 with ducts 65 is molded in an elastomeric material such as latex or silicone rubber and carries a sealing bead 67 which engages hook ring 59 as best illustrated in FIG. 5. Optional liner 69 is fabricated of dipped latex or other material such as a polyethylene film. Bottom 57, inner dome 58 and hook ring 59 may be blow molded as a unit from polypropylene, polyethylene, polyurethane, polystyrene other appropriate thermoplastic, ideally transparent to view the inner contents level. Bottom 57 or inner dome 58 may include markings to indicate fluid contents level. Where liner 69 is to be used, an optional punch out air vent 71 is provided to allow air to enter the container as contents are withdrawn. Liner 69 is collapsible and is sealed at hook ring 59 by compression provided between sealing bead 67 and hook ring 59. Liner 69 in this embodiment is constructed of dipped latex and is washable and reusable. Alternately, liner 69 may be a disposable bag of a material such as polyethylene as is commonly used in disposable bottle liners. The diameter of port 61 may be sized to readily adapt to a standard breast pump. Bottom 57 may optionally include thermographic masking over a warning message (not shown) as discussed above to indicate temperature in the contents.

In operation, liner 69, if used, is simply installed through port 61 and liner bead 73 or a bag top is secured over hook ring 59. The container is filled and sealing bead 67 is stretched over liner bead 73 and hook ring 59 to provide a secure, leak proof seal. It will be obvious to one skilled in the art that the upper extremity of the outer dome 51 or inner dome 58 may be terminated and formed so as to provide annular means as in FIG. 7 which engage a corresponding reinforced annular indent at the base of nipple 63, thereby providing an expansion seal as opposed to the compression seal detailed in FIGS. 4 and 5.

FIG. 5 details the FIG. 4 approach to installing the nipple 63 on a top filling embodiment, and includes a liner 69 with bead 73 engaging hook ring 59 and sealingly compressed by sealing bead 67. Also shown are inner dome 58, outer dome 51, and port 61.

Figure 6:
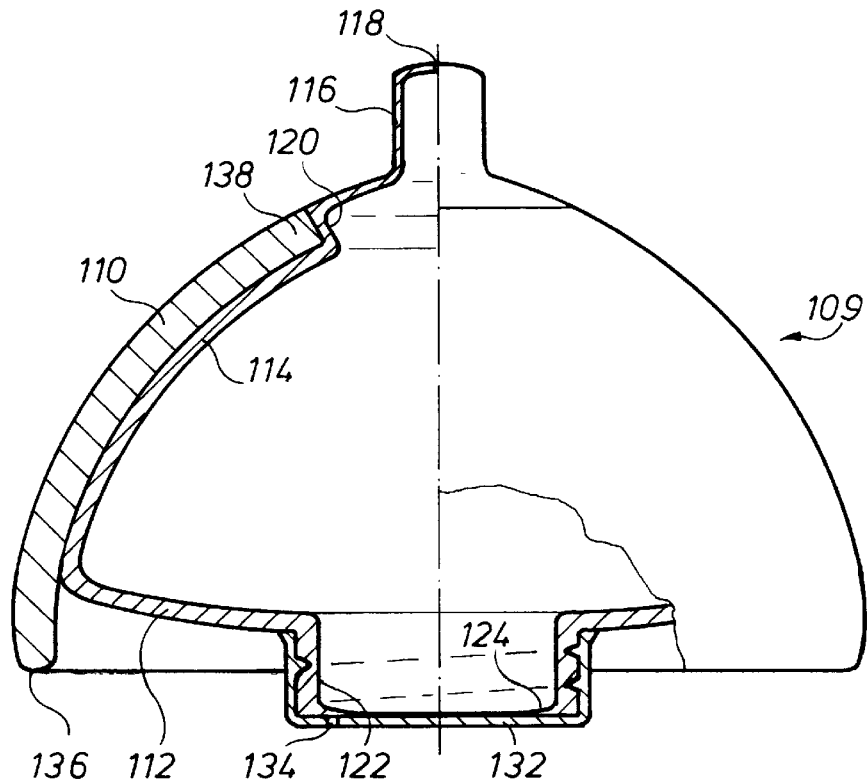
FIG. 6 depicts in partial cross section a three piece container with a foam outer dome.

FIG. 6. discloses a third embodiment, container 109, which includes an outer resilient dome 110 formed in the approximate shape of a breast and constructed of fine celled, resilient foam material such as is described in reference to FIG. 3., above. Bottom 112, with integral inner dome 114, nipple 116 with ducts 118, annular detent 120, and filling port 122 with valvular flange 124 is molded in an elastomer having varying degrees of thickness through the cross section to provide degrees of resilience and rigidity as described above. Current molding technology enables some elastomeric materials to be molded with a degree of controlled variation in wall thickness over the length of the preform or extrusion slug. The FIG. 6 embodiment may avail this technology to create an inner dome 114 which fits snugly within outer dome 110. As in the former embodiments, the extended lower portion of outer dome 110 provides an annular gripping member 136. Threaded lid 132 with air vent 134 seals the closure at port 122 while preventing vacuum build-up in the container as in the embodiment of FIG. 1.

In operation, inner dome 114 is fully inserted into outer dome 110 until nipple engagement shoulder 138 engages annular detent 120. Simultaneously, gripping member 136 contracts to its original diameter to further secure the engagement over inner dome 142. The members may readily be disengaged and reassembled for cleaning and ease of assembly. The resultant container 109 is resilient in the crest portion with excellent tactile quality, yet is rigid enough at bottom 112 and port 124 to retain its shape and to sealably receive threaded lid 132. In these embodiments, annular grasping member 136 is an extension of outer dome 110 and may be formed with a considerable outward or inward flare.

Figure 7:
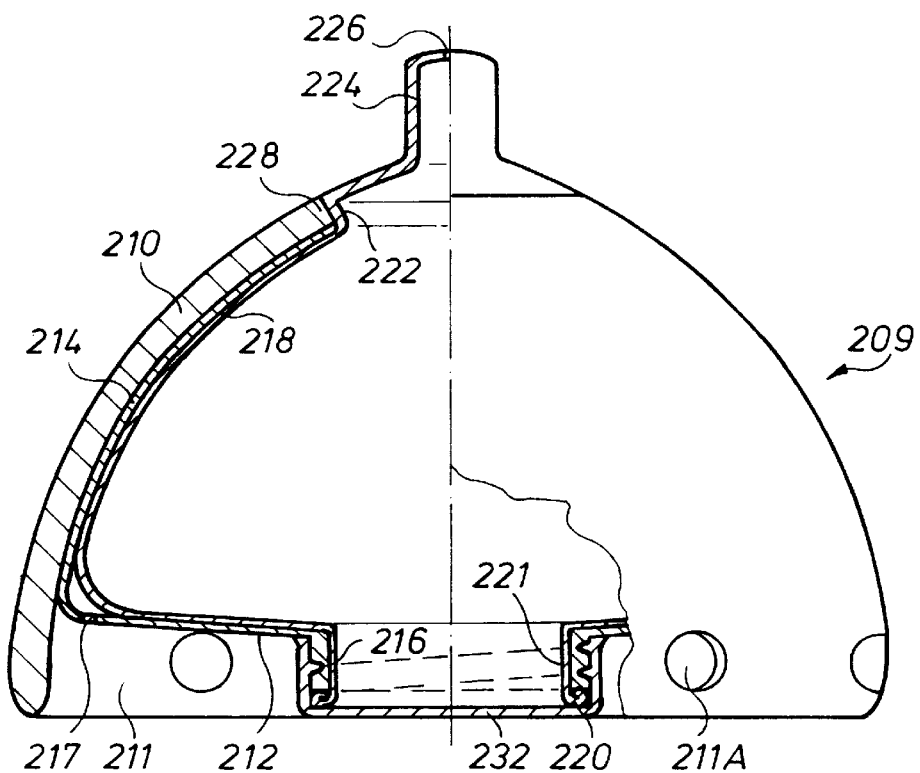
FIG. 7 depicts in partial cross section an additional embodiment which includes a rigid inner dome, a resilient outer dome and a removable bag liner.

Referring now to FIG. 7, outer dome 210 of container 209 is formed in the approximate shape of a breast and is molded in fine celled resilient foam. Similar to the embodiments of FIGS. 4 and 6, the lower portion of outer dome 210 is extended to provide gripping means 211 and is optionally perforated with holes 211A or indents to provide additional gripping ability. A somewhat rigid bottom 212 with integral inner dome 214 and threaded port 216 may be blow molded as a unit from polyethylene, polypropylene, polyurethane, polystyrene, polycarbonate or other appropriate material. Bottom 212 ideally is a transparent thermoplastic to view the inner contents of the container. Air vent 217 permits air to enter the void between inner dome 214 and liner 218 as the contents are withdrawn. Liner 218 has a sealing flange 220, tubular filling portion 221, nipple 224 with ducts 226 and annular detent 222 at the base of nipple 224 to engage a corresponding shoulder 228 comprising the periphery of the upper opening in outer dome 210. Liner 218 in this embodiment is constructed of latex, double dipped at the nipple end and rolled to provide sealing flange 220 at the filling port defined by threaded port 216. Wall thickness in the main body of liner 218 can approximate 0.020" thickness (a single dip) to provide some shape memory, whereas nipple 224 and annular detent 222 should be molded to approximately 0.050" (double dipped) adequate to resist tearing and to provide secure engagement between annular detent 222 and shoulder 228. Threaded port 216 is sized to receive a standard breast pump. Sealing flange 220 fits over the end of threaded port 216 to provide sealing means for the liner contents when threaded lid 232 is securely installed.

Outer dome 210 is stretched to receive bottom 212 and inner dome 214 and may be secured in place by compression, adhesive or other suitable means. In operation, nipple 224 with integral liner 218 is first inserted through port 216 and is thereafter drawn up through the upper opening in outer dome 210 defining shoulder 228 until annular detent 222 of liner 218 is fully engaged by shoulder 228. Liner sealing flange 220 is placed over the end of port 216, whereupon the liner is filled with liquid contents and threaded cap 232 is installed to seal the container for use. The infant user experiences a sculpted, warm, soft surface having skin-like tactile quality without hard or angular surfaces in contact with her face.

RAMIFICATIONS AND SCOPE

Many alternatives exist for the construction of a breast shaped container, including an offset nipple, nuances of shape, types of closure and means of attachment for the nipple and base elements, modified or appended gripping means, various liners and methods of installation, and other adjustments within the scope of the invention. It is therefore intended that the drawings simply depict selected embodiments of a breast-like infant feeding container, thereby expanding upon the disclosure in application Ser. No. 07/814,565. The drawings and specifications, while teaching construction of these embodiments, should not be construed to narrow the claims which more fully delineate the scope of the invention claimed herein. The invention principally attempts to imitate the comforting sensory experience of natural breast feeding. While the formulation of new materials and processes may enable enhanced future designs, the claims anticipate such evolution, permitting appropriate design alternatives within the broader scope.

I claim:

1. An infant feeding container where said container substantially imitates a human female breast in form and function, said container comprising a dome shaped member including a pliant outer surface, said dome shaped member substantially defining a volumetric space adequate to contain from four to eleven ounces of liquids, said dome shaped member having the approximate form of a human female breast including an upper crest portion and a lower skirt portion, said skirt portion being not less than seven centimeters in diameter at its outermost circumference, a ducted nipple protruding from said crest portion of said dome shaped member, and a bottom closure, said bottom closure including means to secure said bottom closure relative to said dome shaped member adjacent to said skirt portion, said bottom closure closing said volumetric space defined by said dome shaped member.

2. The infant feeding container of claim 1 wherein said dome shaped member comprises outer and inner dome shaped members, said outer dome shaped member having an interior surface and said inner dome shaped member having an exterior surface which substantially conforms to said interior surface.

3. The infant feeding container of claim 2, wherein said outer dome shaped member is fabricated of a soft material selected from a list including resilient foam, animal hide, natural and synthetic fibers, quilted down, and fleece.

4. The infant feeding container of claim 2, wherein said bottom closure means is integral with said inner dome shaped member.

5. The infant feeding container of claim 2 further including a replaceable fluid contents liner which is received within said volumetric space.

6. The infant feeding container of claim 1, further including a removable fluid containment liner.

7. The infant feeding container of claim 1, wherein said lower skirt portion extends below said volumetric space to form annular gripping means.

8. The infant feeding container of claim 1, wherein said bottom closure includes means to engage said lower skirt portion and means to provide annular gripping means.

9. The infant feeding container of claim 1, further including valvular means to reduce or eliminate vacuum conditions within said container.

10. The infant feeding container of claim 1, wherein said dome shaped member is composed of a thermoplastic, elastomer, thermoset rubber, silicone rubber, latex, resilient foam material, or other pliant material.

11. The infant feeding container of claim 1 where said container further includes on its surface a temperature warning message and an opaque thermographic mask covering said warning message, said thermographic mask becoming transparent above the optimum safe serving temperature.

12. The infant feeding container of claim 1, wherein said base includes a graspable annular member which is more rigid than said dome shaped member and which forms a gripping means suitable for an infant's fingertips, said container further including means for securing said graspable member and said lower skirt portion of said dome shaped member to said base to provide a closed interior space for holding liquids.

13. The infant feeding container of claim 1, further including a cap which covers said ducted nipple and at least a portion of said dome shaped member.

14. The infant feeding container of claim 13, wherein said cap includes a surface which engages the outer circumference of said container while simultaneously engaging said ducted nipple to close said nipple ducts.

15. The container of claim 1, wherein said crest portion includes an opening, said opening including annular engagement means, said nipple including corresponding annular engagement means to removeably retain said nipple in position relative to said crest portion.

16. The container of claim 1, including an opening therein sized to be directly coupled with a breast pump.

17. A removable fluid contents liner for use in a breast like infant feeding container, said feeding container having a volumetric space for liquid contents substantially defined by a dome shaped member, said dome shaped member including an annular opening at the crest of said dome shaped member, said liner including an integral nipple and means to engage said annular opening to keep said nipple in alliance with said dome shaped member during use.

18. The fluid contents liner of claim 17, wherein said means to engage said annular opening comprises a radial cam member contiguous with said nipple, said radial cam member being engaged with the circumference of said annular opening.

19. The fluid contents liner of claim 17, wherein said liner is latex, silicone rubber or other non-porous material suitable for food contact.

20. The fluid contents liner of claim 17, wherein said liner is retained at said annular opening by means of compression between said nipple and the wall of said annular opening.

* * * * *